(12) United States Patent
El Ali et al.

(10) Patent No.: US 11,192,912 B1
(45) Date of Patent: Dec. 7, 2021

(54) SYNTHESIS OF BIARYL KETONES AND BIARYL DIKETONES VIA CARBONYLATIVE SUZUKI-MIYAURA COUPLING REACTIONS CATALYZED BY BRIDGED BIS(N-HETEROCYCLIC CARBENE)PALLADIUM(II) CATALYSTS

(71) Applicants: King Fahd University of Petroleum & Minerals, Dhahran (SA); Saudi Arabian Oil Company, Dhahran (SA)

(72) Inventors: Bassam El Ali, Dhahran (SA); Waseem Mansour, Dhahran (SA); Mohammed Fettouhi, Dhahran (SA)

(73) Assignee: King Fahd University of Petroleum & Minerals, Dhahran (SA)

( * ) Notice: Subject to any disclaimer, the term of this patent is extended or adjusted under 35 U.S.C. 154(b) by 0 days.

(21) Appl. No.: 17/071,381

(22) Filed: Oct. 15, 2020

(51) Int. Cl.
C07F 15/00 (2006.01)
(52) U.S. Cl.
CPC ................... C07F 15/006 (2013.01)
(58) Field of Classification Search
None
See application file for complete search history.

(56) References Cited

U.S. PATENT DOCUMENTS

| | | | |
|---|---|---|---|
| 2007/0073055 | A1 | 3/2007 | Organ et al. |
| 2009/0326237 | A1 | 12/2009 | Strassner et al. |
| 2019/0016741 | A1 | 1/2019 | Hollis et al. |
| 2019/0374933 | A1 | 12/2019 | Nolan |

OTHER PUBLICATIONS

Avery, K. et al. Tetrahedron Letters, 50 (2009) 2851-2853.*
Aktaş et al., "Mixed phosphine/N-heterocyclic carbene-palladium complexes: synthesis, characterization, crystal structure and application in the Sonogashira reaction in aqueous media." Transition Metal Chemistry 44.3, 2019, 229-236, 8 pages.
Aktaş et al., "Novel morpholine liganded Pd-based N-heterocyclic carbene complexes: Synthesis, characterization, crystal structure, antidiabetic and anticholinergic properties." Polyhedron 159, 2019, 345-354, 32 pages.
Bai, Cuihua, et al. "Carbonylative Sonogashira coupling of terminal alkynes with aryl iodides under atmospheric pressure of CO using Pd (II) MOF as the catalyst." Catalysis Science & Technology 4.9, 2014, 3261-3267, 7 pages.
Brennführer et al., "Palladium-catalyzed carbonylation reactions of aryl halides and related compounds." Angewandte Chemie International Edition 48.23, 2009, 4114-4133, 20 pages.
Cui et al., "Carbonylative Suzuki coupling reactions of aryl iodides with arylboronic acids over Pd/SiC." Chinese Journal of Catalysis 36.3, 2015, 322-327, 6 pages.
Feng et al., "Carbonylative Sonogashira Coupling of Aryl Iodides with Terminal Alkynes Catalyzed by Palladium Nanoparticles." Journal of the Chinese Chemical Society 65.3, 2018, 337-345.

Gadge et al., "Recent developments in palladium catalysed carbonylation reactions." RSC Advances 4.20, 2014, 10367-10389, 23 pages.
Gautam et al., "Aminophosphine Palladium Pincer-Catalyzed Carbonylative Sonogashira and Suzuki-Miyaura Cross-Coupling with High Catalytic Turnovers." ACS omega 4.1, 2019, 1560-1574, 15 pages.
Gautam et al., "Palladacycle-Catalyzed Carbonylative Suzuki-Miyaura Coupling with High Turnover Number and Turnover Frequency." The Journal of organic chemistry 80.15, 2015, 7810-7815, 19 pages.
Genelot et al., "Carbonylative Sonogashira coupling in the synthesis of ynones: a study of "boomerang" phenomena." Advanced Synthesis & Catalysis 355.13, 2013, 2604-2616, 14 pages.
He et al., "Highly enantioselective azadiene Diels—Alder reactions catalyzed by chiral N-heterocyclic carbenes." Journal of the American Chemical Society 128.26, 2006, 8418-8420, 3 pages.
Hopkinson et al., "An overview of N-heterocyclic carbenes." Nature 510.7506, 2014, 485-496, 12 pages.
Huynh et al., "Syntheses and catalytic activities of Pd (II) dicarbene and hetero-dicarbene complexes." Journal of Organometallic Chemistry 696.21, 2011, 3369-3375, 7 pages.
Ibrahim et al., "Efficient N-heterocyclic carbene palladium (II) catalysts for carbonylative Suzuki-Miyaura coupling reactions leading to aryl ketones and diketones." Journal of Organometallic Chemistry 859, 2018, 44-51, 21 pages.
Ibrahim et al., "Novel (N-heterocyclic carbene) Pd (pyridine) Br2 complexes for carbonylative Sonogashira coupling reactions: Catalytic efficiency and scope for arylalkynes, alkylalkynes and dialkynes." Applied Organometallic Chemistry 32.4, 4280, 2018, 1.
Ibrahim et al., "Synthesis, crystal structures and catalytic activities of new palladium (II)—bis (oxazoline) complexes." Transition Metal Chemistry 41.7, 2016, 739-749.
Ishiyama et al., "Synthesis of unsymmetrical biaryl ketones via palladium-catalyzed carbonylative cross-coupling reaction of arylboronic acids with iodoarenes." Tetrahedron letters 34.47, 1993, 7595-7598, 4 pages.
Kang et al., "Pd (0)—Cu (I)-catalyzed cross-coupling of alkynylsilanes with triarylantimony (V) diacetates." Journal of the Chemical Society, Perkin Transactions 1 7 (2001): 736-739, 4 pages.
Ketike et al., "Carbonylative Suzuki-Miyaura cross-coupling over Pd NPs/Rice-Husk carbon-silica solid catalyst: Effect of 1, 4-dioxane solvent." ChemistrySelect 3.25, 2018, 7164-7169, 6 pages.
Kobayash et al., "Carbonylation of organic halides in the presence of terminal acetylenes; novel acetylenic ketone synthesis." Journal of the Chemical Society, Chemical Communications 7, 1981, 333-334, 2 pages.
Kostyukovich et al., "In situ transformations of Pd/NHC complexes with N-heterocyclic carbene ligands of different nature into colloidal Pd nanoparticles." Inorganic Chemistry Frontiers 6.2, 2019, 482-492, 11 pages.

(Continued)

*Primary Examiner* — Clinton A Brooks
(74) *Attorney, Agent, or Firm* — Fish & Richardson P.C.

(57) ABSTRACT

This disclosure relates to bridged bis(N-heterocyclic carbene)palladium(II) complexes, methods of preparing the complexes, and methods of using the complexes in Suzuki-Miyaura coupling reactions.

21 Claims, No Drawings

(56) References Cited

OTHER PUBLICATIONS

Kumar et al., "Stereoelectronic Profiling of Expanded-Ring N-Heterocyclic Carbenes." Inorganic chemistry 58.11, 2019, 7545-7553, 9 pages.
Lee et al., "Carbonylative Coupling of 4, 4'-Diiodobiphenyl Catalyzed by Pd (NHC) Complex.", 2013, 4 pages.
Liang et al., "Pd-catalyzed copper-free carbonylative Sonogashira reaction of aryl iodides with alkynes for the synthesis of alkynyl ketones and flavones by using water as a solvent." The Journal of organic chemistry 70.15, 2005, 6097-6100, 4 pages.
Liu et al., "Magnetically separable Pd catalyst for carbonylative sonogashira coupling reactions for the synthesis of α, β-alkynyl ketones." Organic letters 10.18, 2008, 3933-3936, 4 pages.
Ma et al., "N-Heterocyclic carbene-stabilized palladium complexes as organometallic catalysts for bioorthogonal cross-coupling reactions." The Journal of organic chemistry 79.18, 2014, 8652-8658, 7 pages.
Mingji, Dai, et al. "A novel thiourea ligand applied in the Pd-catalyzed Heck, Suzuki and Suzuki carbonylative reactions." Advanced Synthesis & Catalysis 346.13-15, 2004, 1669-1673, 5 pages.
Mohamed et al., "Carbonylative sonogashira coupling of terminal alkynes with aqueous ammonia." Organic letters 5.17 (2003): 3057-3060, 4 pages.
Nelson et al., "Quantifying and understanding the electronic properties of N-heterocyclic carbenes." Chemical Society Reviews 42.16, 2013, 6723-6753, 31 pages.
Nguyen et al., "Postmodification Approach to Charge-Tagged 1, 2, 4-Triazole-Derived NHC Palladium (II) Complexes and Their Applications." Organometallics 36.12, 2017, 2345-2353, 9 pages.
Niu, Jian-Rui, et al. "Preparation of Recoverable Pd Catalysts for Carbonylative Cross-Coupling and Hydrogenation Reactions." ChemCatChem 5.1 (2013): 349-354, 6 pages.
Niu, Jianrui, et al. "Stabilizing Pd II on hollow magnetic mesoporous spheres: a highly active and recyclable catalyst for carbonylative cross-coupling and Suzuki coupling reactions." New Journal of Chemistry 38.4, 2014, 1471-1476, 6 pages.
O'Keefe et al., "Carbonylative Cross-Coupling of ortho-Disubstituted Aryl Iodides. Convenient Synthesis of Sterically Hindered Aryl Ketones." Organic letters 10.22, 2008, 5301-5304, 4 pages.
Park et al., "Pd-catalyzed carbonylative reactions of aryl iodides and alkynyl carboxylic acids via decarboxylative couplings." Organic Letters 13.5, 2011, 944-947, 4 pages.
Rajabi et al., "An Efficient Palladium N-Heterocyclic Carbene Catalyst Allowing the Suzuki-Miyaura Cross-Coupling of Aryl Chlorides and Arylboronic Acids at Room Temperature in Aqueous Solution," Advanced Synthesis & Catalysis 356.8, 2014, 1873-1877, 5 pa.
Sakaguchi et al., "Chiral Palladium (II) Complexes Possessing a Tridentate N-Heterocyclic Carbene Amidate Alkoxide Ligand: Access to Oxygen-Bridging Dimer Structures." Angewandte Chemie International Edition 47.48, 2008, 9326-9329, 4 pages.
Schmid et al., "Mixed phosphine/N-heterocyclic carbene palladium complexes: Synthesis, characterization and catalytic use in aqueous Suzuki-Miyaura reactions." Dalton Transactions 42.20, 2013, 7345-7353, 9 pages.
Tambade et al., "Copper-Catalyzed, Palladium-Free Carbonylative Sonogashira Coupling Reaction of Aliphatic and Aromatic Alkynes with Iodoaryls." Synlett 2008.06, 2008, 886-888, 3 pages.
Tambade et al., "Phosphane-Free Palladium-Catalyzed Carbonylative Suzuki Coupling Reaction of Aryl and Heteroaryl Iodides." European Journal of Organic Chemistry 2009.18, 2009, 3022-3025, 4 pages.
Tao et al., "Palladium complexes bearing an N-heterocyclic carbene-sulfonamide ligand for cooligomerization of ethylene and polar monomers." Journal of Polymer Science Part A: Polymer Chemistry 57.3, 2019, 474-477, 4 pages.
Taylor et al., "Metal-free Synthesis of Ynones from Acyl Chlorides and Potassium Alkynyltrifluoroborate Salts." JoVE (Journal of Visualized Experiments) 96, e52401, 2015, 9 pages.
Touj et al., "Correction: Efficient in situ N-heterocyclic carbene palladium (ii) generated from Pd (OAc) 2 catalysts for carbonylative Suzuki coupling reactions of arylboronic acids with 2-bromopyridine under inert conditions leading to unsymmetrical arylpyridine ketones: synthesis, characterization and cytotoxic activities." RSC Advances 9.2, 2019, 16 pages.
Wang et al., "Carbonylative Suzuki cross-coupling reaction catalyzed by bimetallic Pd—Pt nanodendrites under ambient CO pressure." Catalysis Communications 101, 2017, 10-14, 21 pages.
Wang et al., "Cross-linked polymer supported palladium catalyzed carbonylative Sonogashira coupling reaction in water." Tetrahedron letters 52.14, 2011, 1587-1591, 5 pages.
Wang et al., "N-heterocyclic carbene-palladium (II) complexes with benzoxazole or benzothiazole ligands: Synthesis, characterization, and application to Suzuki-Miyaura cross-coupling reaction." Journal of Organometallic Chemistry 804, 2016, 73-79, 24 page.
Wu et al., "A General Palladium-Catalyzed Carbonylative Sonogashira Coupling of Aryl Triflates." Chemistry—A European Journal 17.1, 2011, 106-110, 5 pages.
Wu et al., "Palladium-catalyzed carbonylative coupling of benzyl chlorides with terminal alkynes to give 1, 4-diaryl-3-butyn-2-ones and related furanones." Organic & Biomolecular Chemistry 9.23, 2011, 8003-8005, 3 pages.
Zhang et al., "Aryl-palladium-NHC complex: efficient phosphine-free catalyst precursors for the carbonylation of aryl iodides with amines or alkynes." Organic & Biomolecular Chemistry 12.47, 2014, 9702-9706, 5 pages.
Zhang et al., "Chiral linker-bridged bis-N-heterocyclic carbenes: design, synthesis, palladium complexes, and catalytic properties." Dalton Transactions 45.29, 2016, 11699-11709, 14 pages.
Zheng et al., "Highly efficient N-Heterocyclic carbene-palladium complex-catalyzed multicomponent carbonylative Suzuki reaction: novel practical synthesis of unsymmetric aryl ketones." Applied Organometallic Chemistry 21.9, 2007, 772-776, 5 pages.
Zhiping et al., "Synthesis of propylene carbonate from alcoholysis of urea catalyzed by modified hydroxyapatites." Chinese Journal of Catalysis 31.4, 2010, 3 pages.
Awuah et al., Access to Flavones via a Microwave-Assisted, One-Pot Sonogashira-Carbonylation-Annulation Reaction Org. Lett. vol. 11, 2009, 3210-3213, 4 pages.
Babu et al., "Synthesis and biological evaluation of novel 8-aminomethylated oroxylin A analogues as alpha-glucosidase inhibitors." Bioorganic & medicinal chemistry letters 18.5, 2008, 1659-1662, 4 pages.
Baruah et al., "Ru (ii)-Catalyzed C—H activation and annulation of salicylaldehydes with monosubstituted and disubstituted alkynes." Chemical Communications 52.88, 2016, 13004-13007, 4 pages.
Boncel et al., "Michael-type addition of azoles of broad-scale acidity to methyl acrylate." Beilstein journal of organic chemistry 7.1, 2011, 173-178, 6 pages.
Brimble et al., "Pyrans and their Benzo Derivatives: Synthesis." Comprehensive Heterocyclic Chemistry III, 2008, 281 pages.
Chinchilla et al., "The Sonogashira reaction: a booming methodology in synthetic organic chemistry," Chemical reviews 107.3, 2007, 874-922.
Demirayak et al., "New chroman-4-one/thiochroman-4-one derivatives as potential anticancer agents." Saudi Pharmaceutical Journal 25.7,2017, 1063-1072, 31 pages.
Ferreira et al., "Flavonoid compounds as reversal agents of the P-glycoprotein-mediated multidrug resistance: biology, chemistry and pharmacology." Phytochemistry Reviews 14.2, 2015, 233-272, 40 pages.
Gazvoda et al., "A mesoionic bis (Py-tz NHC) palladium (ii) complex catalyses "green" Sonogashira reaction through an unprecedented mechanism." Chemical Communications 52.8, 2016, 1571-1574, 4 pages.
Hahn et al., "The Pd (II) complex of a bidentate di (benzimidazol-2-ylidene) ligand." Zeitschrift für Naturforschung B 59.5, 2004, 541-543, 3 pages.
Hao et al., "The first heterogeneous carbonylative Sonogashira coupling reaction catalyzed by MCM-41-supported bidentate phosphine palladium (0) complex." Journal of Molecular Catalysis A: Chemical 298.1-2, 2009, 94-98, 5 pages.

(56) References Cited

OTHER PUBLICATIONS

Harvey et al., "A new chromone and flavone synthesis and its utilization for the synthesis of potentially antitumorigenic polycyclic chromones and flavones." The Journal of Organic Chemistry 55.25, 1990, 6161-6166, 6 pages.
Hostetler et al., "Flavones: Food sources, bioavailability, metabolism, and bioactivity." Advances in Nutrition 8.3, 2017, 423-435, 13 pages.
Islam et al., "Potent α-glucosidase and protein tyrosine phosphatase 1B inhibitors from Artemisia capillaris." Archives of pharmacal research 36.5, 2013, 542-552, 11 pages.
Ismail et al., "Synthesis and biological evaluation of some novel 4H-benzopyran-4-one derivatives as nonsteroidal antiestrogens." European journal of medicinal chemistry 36.3, 2001, 243-253, 11 pages.
Jagadeesan et al., "The nature of Pd-carbene and Pd-halogen bonds in (bisNHC) PdX 2 type catalysts: insights from density functional theory," RSC advances 5.98, 2015, 80661-80667, 7 pages.
Kabalka et al., "Microwave-assisted synthesis of functionalized flavones and chromones." Tetrahedron Letters 46.37, 2005, 6315-6317, 3 pages.
Keri et al., "Chromones as a privileged scaffold in drug discovery: A review." European journal of medicinal chemistry 78, 2014, 340-374, 35 pages.
Kim et al., "Unified approach to (thio) chromenones via one-pot Friedel-Crafts acylation/cyclization: Distinctive mechanistic pathways of β-chlorovinyl ketones." Organic letters 19.2, 2017, 312-315, 4 pages.
Liu et al., "Construction of the flavones and aurones through regioselective carbonylative annulation of 2-bromophenols and terminal alkynes." Tetrahedron Letters 54.14, 2013, 1802-1807, 6 pages.
Maiti et al., "Synthesis and cancer chemopreventive activity of zapotin, a natural product from Casimiroa edulis." Journal of medicinal chemistry 50.2, 2007, 350-355, 6 pages.
Mansour et al., "Novel and efficient bridged bis (N-heterocyclic carbene) palladium (II) catalysts for selective carbonylative Suzuki-Miyaura coupling reactions to biaryl ketones and biaryl diketones." Applied Organometallic Chemistry 34.6, e5636, 2020, 20 pages.
Miao et al., "Regiospecific carbonylative annulation of iodophenol acetates and acetylenes to construct the flavones by a new catalyst of palladium-thiourea-dppp complex." Organic letters 2.12, 2000, 1765-1768, 4 pages.
Mohapatra et al., "Michael Addition of Imidazole to α, β-Unsaturated Carbonyl/Cyano Compound." Open Chemistry Journal 5.1, 2018, 14 pages.
Morimoto et al., "Insect antifeedant activity of flavones and chromones against Spodoptera litura." Journal of agricultural and food chemistry 51.2, 2003, 389-393, 5 pages.
Muskawar et al., "NHC-metal complexes based on benzimidazolium moiety for chemical transformation: 1st Cancer Update." Arabian Journal of Chemistry 9, 2016, S1765-S1778, 14 pages.
Musthafa et al., "Microwave-assisted solvent-free synthesis of biologically active novel heterocycles from 3-formylchromones." Medicinal Chemistry Research 20.9, 2011,1473-1481, 9 pages.
Netzer et al., "The actual role of sodium cromoglycate in the treatment of asthma—a critical review." Sleep and Breathing 16.4, 1027-1032, 2012, 6 pages.

Qi et al., "Selective palladium-catalyzed carbonylative synthesis of aurones with formic acid as the CO source." RSC advances 6.67,2016, 62810-62813, 4 pages.
Rueping et al., "A review of new developments in the Friedel-Crafts alkylation—From green chemistry to asymmetric catalysis." Beilstein journal of organic chemistry 6.1, 2010, 24 pages.
Sartori et al., Advances in Friedel-Crafts Acy/ation Reactions: Catalytic and Green Processes book 1st Edition, 2009, 222 pages.
Taniguchi, "Aerobic nickel-catalyzed hydroxysulfonylation of alkenes using sodium sulfinates." The Journal of organic chemistry 80.15, 2015, 7797-7802, 20 pages.
Wu et al., "Palladium-Catalyzed Carbonylation Reaction of Aryl Bromides with 2-Hydroxyacetophenones to Form Flavones." Chemistry—A European Journal 18.40, 2012, 12595-12598, 5 pages.
Xu et al., "Divergent synthesis of flavones and aurones via base-controlled regioselective palladium catalyzed carbonylative cyclization," Molecular Catalysis 452, 2018, 264-270, 7 pages.
Xue et al., "Pd-carbene catalyzed carbonylation reactions of aryl iodides." Dalton Transactions 40.29, 2011, 7632-7638, 7 pages.
Yang et al., "Pd catalyzed couplings of "superactive esters" and terminal alkynes: Application to flavones and γ-benzopyranones construction." Journal of Molecular Catalysis A: Chemical 426, 2017, 24-29, 6 pages.
Yang et al., "Synthesis of chromones via palladium-catalyzed ligand-free cyclocarbonylation of o-iodophenols with terminal acetylenes in phosphonium salt ionic liquids." The Journal of organic chemistry 75.3, 2010, 948-950, 3 pages.
Yaşar et al., "Microwave-Assisted Synthesis of 4'-Azaflavones and Their N-Alkyl Derivatives with Biological Activities." Chemistry & biodiversity 5.5, 2008, 830-838, 9 pages.
Yoshida et al., "A concise total synthesis of biologically active frutinones via tributylphosphine-catalyzed tandem acyl transfer-cyclization," Tetrahedron 70.21, 2014, 3452-3458, 7 pages.
Zhang et al., "Enantioselective formal [4+2] annulation of ortho-quinone methides with ortho-hydroxyphenyl α, β-unsaturated compounds." The Journal of organic chemistry 83.17, 2018, 10175-10185, 11 pages.
Zhao et al., "C—H functionalization via remote hydride elimination: Palladium catalyzed dehydrogenation of ortho-acyl phenols to flavonoids." Organic letters 19.5, 2017, 976-979, 4 pages.
Zhao et al., "Synthesis and insecticidal activity of chromanone and chromone analogues of diacylhydrazines." Bioorganic & medicinal chemistry 15.5, 2007, 1888-1895, 8 pages.
Zhiping et al., "Transition-Metal-Catalyzed Carbonylative Synthesis and Functionalization of Heterocycles." Chinese Journal of Organic Chemistry 39.3, 2019, 573-590, 18 pages.
Zhong et al., "An efficient synthesis of 4-chromanones." Tetrahedron letters 52.38, 2011, 4824-4826, 3 pages.
Zhou et al., "Synthesis of indoles through Palladium-catalyzed three-component reaction of aryl iodides, alkynes, and diaziridinone." Organic letters 20.20, 2018, 6440-6443, 4 pages.
Zhu et al., "Highly efficient synthesis of flavones via Pd/C-catalyzed cyclocarbonylation of 2-iodophenol with terminal acetylenes." Catalysis Science & Technology 6.9, 2016, 2905-2909,4 pages.
U.S. Appl. No. 17/071,713, Ali et al., filed Oct. 15, 2020.
U.S. Appl. No. 17/094,140, Ali et al., filed Nov. 10, 2020.

* cited by examiner

SYNTHESIS OF BIARYL KETONES AND BIARYL DIKETONES VIA CARBONYLATIVE SUZUKI-MIYAURA COUPLING REACTIONS CATALYZED BY BRIDGED BIS(N-HETEROCYCLIC CARBENE)PALLADIUM(II) CATALYSTS

TECHNICAL FIELD

This document relates to use of bridged bis(N-heterocyclic carbene)palladium(II) complexes in carbonylative Suzuki-Miyaura coupling reactions to form biaryl ketones and biaryl diketones.

BACKGROUND

Biaryl ketones and biaryl diketones have utility as synthetic intermediates, particularly for the synthesis of heterocyclic systems that can be used as precursors in the synthesis of dyes and liquid crystals for electronic displays. Biaryl ketones and biaryl diketones have also found use in the polymer industry. A common route for the synthesis of these compounds is the carbonylative Suzuki-Miyaura coupling reaction. The reaction is typically catalyzed by a palladium complex but requires high catalyst loading, for example, greater than 1 mol % of the palladium complex is often required. This can lead to higher costs and less efficient reactions.

Therefore, there is a need for a palladium complex that can catalyze a Suzuki-Miyaura coupling reaction, in particular, a carbonylative Suzuki-Miyaura coupling reaction, that has high catalytic activity, is stable, and requires low catalyst loading. There is also a need for an efficient method of using the Suzuki-Miyaura carbonylative coupling reaction to produce biaryl ketones and biaryl diketones.

SUMMARY

Provided in the present disclosure is a method of preparing a biaryl ketone, the method comprising contacting an aryl halide and an aryl boronic acid with a compound of Formula (I) in the presence of a CO source, wherein the compound of Formula (I) has the structure:

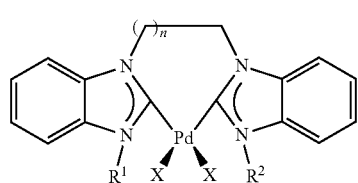

(I)

wherein:

$R^1$ and $R^2$ are each independently selected from $C_1$-$C_{10}$ alkyl, $C_1$-$C_{10}$ haloalkyl, $C_3$-$C_{10}$ cycloalkyl, aryl, 5-7 membered heteroaryl, 5-7 membered heterocycloalkyl, ($C_1$-$C_3$ alkylene)-($C_3$-$C_{10}$ cycloalkyl), ($C_1$-$C_3$ alkylene)-aryl, ($C_1$-$C_3$ alkylene)-(5-7 membered heteroaryl), and ($C_1$-$C_3$ alkylene)-(5-7 membered heterocycloalkyl);

X is selected from Cl, Br, and I; and n is 1 to 4.

In some embodiments of the method, $R^1$ and $R^2$ are each independently $C_1$-$C_6$ alkyl. In some embodiments, $R^1$ and $R^2$ are each independently selected from methyl, ethyl, propyl, isopropyl, and butyl. In some embodiments, $R^1$ and $R^2$ are each isopropyl.

In some embodiments of the method, X is Br.

In some embodiments of the method, n is 1. In some embodiments, n is 2. In some embodiments, n is 3.

In some embodiments of the method, the compound of Formula (I) is selected from:

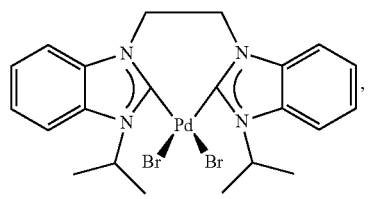

,

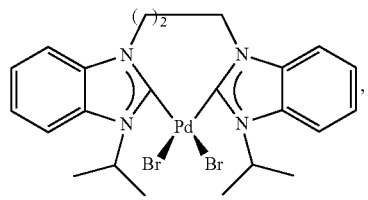

, and

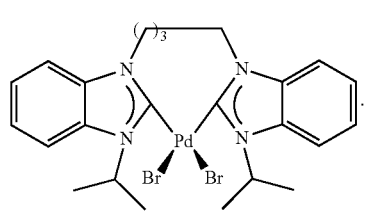

.

In some embodiments of the method, the aryl halide is a compound having the formula:

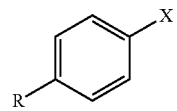

wherein:

X is selected from F, Cl, Br, and I; and

R is selected from H, $C_1$-$C_6$ alkyl, $C_1$-$C_6$ haloalkyl, —O—($C_1$-$C_6$ alkyl), aryl, CN, $NO_2$, —C(=O)H, and —C(=O)($C_1$-$C_6$ alkyl).

In some embodiments of the method, X is I. In some embodiments, X is Br.

In some embodiments of the method, R is selected from H, $C_1$-$C_3$ alkyl, $C_1$-$C_3$ haloalkyl, —O—($C_1$-$C_3$ alkyl), CN, $NO_2$, —C(=O)H, and —C(=O)($C_1$-$C_3$ alkyl). In some embodiments, R is selected from H, methyl, trifluoromethyl, —O—$CH_3$, CN, $NO_2$, —C(=O)H, and —C(=O)($CH_3$).

In some embodiments of the method, the aryl boronic acid is a compound having the formula:

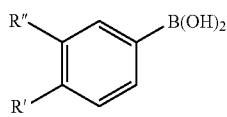

wherein:

R' is selected from H, $C_1$-$C_6$ alkyl, aryl, and —O—($C_1$-$C_6$ alkyl);

R" is selected from H, $C_1$-$C_6$ alkyl, aryl, and —O—($C_1$-$C_6$ alkyl); or

R' and R", taken together with the carbon atoms to which they are attached, form a 5-7 membered heterocycloalkyl ring.

In some embodiments of the method, R' is selected from H and —O—$CH_3$.

In some embodiments of the method, R" is H.

In some embodiments of the method, R' and R", taken together with the carbon atoms to which they are attached, form a 5-membered heterocycloalkyl ring containing 2 oxygen atoms.

In some embodiments of the method, the biaryl ketone is a compound having the formula:

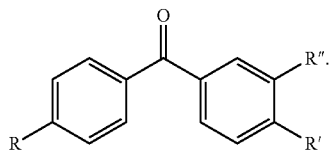

In some embodiments of the method, the compound of Formula (I) is present in an amount of about 0.001 mol % to about 1.0 mol %. In some embodiments, the compound of Formula (I) is present in an amount of about 0.05 mol % to about 0.015 mol %. In some embodiments, the compound of Formula (I) is present in an amount of about 0.01 mol %.

DETAILED DESCRIPTION

The present disclosure relates to N,N'-substituted bisbenzimidazolium salts and bridged bis(N-heterocyclic carbene) palladium(II) complexes and the use of the bridged bis(N-heterocyclic carbene)palladium(II) complexes in chemical reactions to produce biaryl ketones and biaryl diketones. The bridged bis(N-heterocyclic carbene)palladium(II) complexes exhibit high catalytic activity and efficiency with low catalyst loading. For example, the bridged bis(N-heterocyclic carbene)palladium(II) complexes exhibit high catalytic efficiency in the synthesis of biaryl ketones and biaryl diketones via carbonylative Suzuki-Miyaura coupling reactions. Without wishing to be bound by any theory, it is believed that the chelating effect of the bridged bis(N-heterocyclic carbene)palladium(II) complexes contributes strongly to the stability and the catalytic activity of these complexes in the carbonylative Suzuki-Miyaura coupling reactions with a low loading and high turnover number (TON) of catalyst. In some embodiments, the coupling reaction is between an aryl halide or aryl dihalide and an aryl boronic acid or aryl diboronic acid. The resulting biaryl ketones and biaryl diketones can be useful precursors in the synthesis of dyes and liquid crystals for electronic displays. The biaryl ketones and biaryl diketones can also be used in the polymer industry.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Definitions

In this disclosure, the terms "a," "an," and "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (for example, 1%, 2%, 3%, and 4%) and the sub-ranges (for example, 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

The term "about" as used herein can allow for a degree of variability in a value or range, for example, within 10%, within 5%, or within 1% of a stated value or of a stated limit of a range.

In the methods described in the present disclosure, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "cycloalkyl" means a non-aromatic cyclic ring system containing only carbon atoms in the ring system backbone, such as cyclopropyl, cyclobutyl, cyclopentyl, cyclohexyl, and cyclohexenyl. Cycloalkyl may include multiple fused rings. Cycloalkyl may have any degree of saturation provided that none of the rings in the ring system are aromatic. Cycloalkyl groups can either be unsubstituted or substituted with one or more substituents. In some embodiments, cycloalkyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, and 2,3-dihydro-1H-indenyl. In some embodiments, the aryl is phenyl.

As used herein, the term "heteroaryl" means a mono- or bicyclic group having 5 to 10 ring atoms, such as 5, 6, 8, 9, or 10 ring atoms, such as 5, 6, 9, or 10 ring atoms; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrrolo[2,3-6]pyridinyl, quinazolinyl, quinolinyl, thieno[2,3-c]pyridinyl, pyrazolo[3,4-6]pyridinyl, pyrazolo[3,4-c]pyridinyl, pyrazolo[4,3-c]pyridine, pyrazolo[4,3-6]pyridinyl, tetrazolyl, chromane, 2,3-dihydrobenzofuran, tetrahydroquinoline, and isoindoline. In some embodiments, the heteroaryl is selected from thienyl, pyridinyl, furyl, pyrazolyl, imidazolyl, isoindolinyl, pyranyl, pyrazinyl, and pyrimidinyl.

As used herein, "heterocyclyl" means a 3-14 membered, such as 3-11 membered, such as 3-8 membered nonaromatic mono-, bi- or tricyclic group comprising at least one heteroatom in the ring system backbone. Bicyclic and tricyclic heterocyclyl groups may include fused ring systems, spirocyclic ring systems, and bridged ring systems and may include multiple fused rings. In some embodiments, heterocyclyls have one to four heteroatom(s) independently selected from N, O, and S. In some embodiments, heterocyclyls have one to three heteroatom(s) independently selected from N, O, and S. In some embodiments, heterocyclyls have one to two heteroatom(s) independently selected from N, O, and S. In some embodiments, monocyclic heterocyclyls are 3-membered rings. In some embodiments, monocyclic heterocyclyls are 4-membered rings. In some embodiments, monocyclic heterocyclyls are 5-membered rings. In some embodiments, monocyclic heterocyclyls are 6-membered rings. In some embodiments, monocyclic heterocyclyls are 7-membered rings. As used herein, "monocyclic heterocyclyl" means a single nonaromatic cyclic ring comprising at least one heteroatom in the ring system backbone. Examples of heterocyclyls include aziridinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, and thiomorpholinyl. In some embodiments, the heterocyclyl is selected from azetidinyl, morpholinyl, piperazinyl, pyrrolidinyl, and tetrahydropyridinyl. As used herein, "bicyclic heterocyclyl" means a nonaromatic bicyclic ring system comprising at least one heteroatom in the ring system backbone. Examples of bicyclic heterocyclyls include 2-azabicyclo[1.1.0] butane, 2-azabicyclo[2.1.0]pentane, 2-azabicyclo[1.1.1]pentane, 3-azabicyclo[3.1.0] hexane, 5-azabicyclo[2.1.1]hexane, 3-azabicyclo[3.2.0]heptane, 2-oxa-5-azabicyclo[2.2.1]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, and 2-azabicyclo[2.2.2]octane. As used herein, "spirocyclic heterocyclyl" means a nonaromatic bicyclic ring system comprising at least one heteroatom in the ring system backbone and with the rings connected through just one atom. Examples of spirocyclic heterocyclyls include 2-azaspiro[2.2]pentane, 2-oxa-6-azaspiro[3.3]heptane, 4-azaspiro[2.5]octane, 1-azaspiro [3.5]nonane, 2-azaspiro[3.5]nonane, 7-azaspiro[3.5]nonane, 2-azaspiro[4.4]nonane, 6-azaspiro[2.6]nonane, 1,7-diazaspiro[3.5]nonane, 2,7-diazaspiro[3.5]nonane, 1,7-diazaspiro[4.5]decane, 2,5-diazaspiro[3.6]decane, 1-oxa-8-azaspiro[4.5]decane, 2-oxa-8-azaspiro[4.5]decane.

Compounds of Formula (I)

Provided in the present disclosure is a compound of Formula (I)

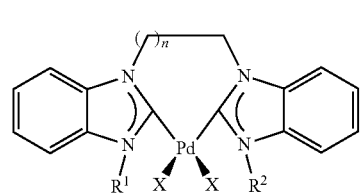

(I)

wherein:

$R^1$ and $R^2$ are each independently selected from $C_1$-$C_{10}$ alkyl, $C_1$-$C_{10}$ haloalkyl, $C_3$-$C_{10}$ cycloalkyl, aryl, 5-7 membered heteroaryl, 5-7 membered heterocycloalkyl, ($C_1$-$C_3$ alkylene)-($C_3$-$C_{10}$ cycloalkyl), ($C_1$-$C_3$ alkylene)-aryl, ($C_1$-$C_3$ alkylene)-(5-7 membered heteroaryl), and ($C_1$-$C_3$ alkylene)-(5-7 membered heterocycloalkyl);

X is selected from Cl, Br, and I; and n is 1 to 4.

In some embodiments of the compound of Formula (I), le is $C_1$-$C_{10}$ alkyl. In some embodiments of the compound of Formula (I), le is $C_1$-$C_6$ alkyl. In some embodiments, le is selected from methyl, ethyl, propyl, isopropyl, and butyl. In some embodiments, le is isopropyl. In some embodiments, the $C_1$-$C_6$ alkyl group is optionally substituted with one or more substituents independently selected from halogen, —CN, —OH, —NH$_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (I), $R^2$ is $C_1$-$C_{10}$ alkyl. In some embodiments of the compound of Formula (I), $R^2$ is $C_1$-$C_6$ alkyl. In some embodiments, $R^2$ is selected from methyl, ethyl, propyl, isopropyl, and butyl. In some embodiments, $R^2$ is isopropyl. In some embodiments, the $C_1$-$C_6$ alkyl group is optionally substituted with one or more substituents independently selected from halogen, —CN, —OH, —NH$_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (I), $R^1$ and $R^2$ are the same. In some embodiments, $R^1$ and $R^2$ are different.

In some embodiments of the compound of Formula (I), $R^1$ and $R^2$ are each independently $C_1$-$C_6$ alkyl. In some embodiments, $R^1$ and $R^2$ are each independently selected from methyl, ethyl, propyl, isopropyl, and butyl. In some embodiments, $R^1$ is isopropyl and $R^2$ is isopropyl.

In some embodiments of the compound of Formula (I), X is selected from Cl, Br, and I. In some embodiments, X is Cl. In some embodiments, X is Br. In some embodiments, X is I.

In some embodiments of the compound of Formula (I), n is 1 to 4. In some embodiments, n is 1. In some embodiments, n is 2. In some embodiments, n is 3. In some embodiments, n is 4.

In some embodiments, the compound of Formula (I) is selected from:

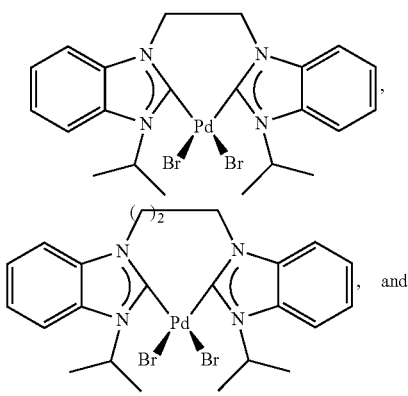

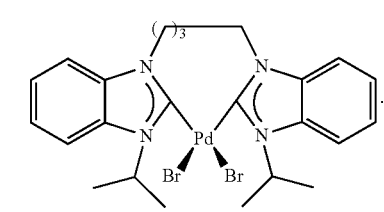

In some embodiments, the compound of Formula (I) is

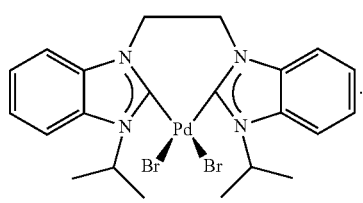

In some embodiments, the compound of Formula (I) is

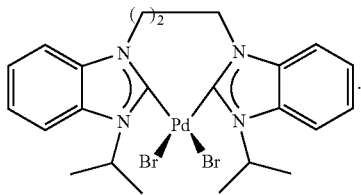

In some embodiments, the compound of Formula (I) is

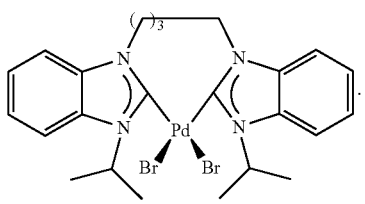

Compounds of Formula (II)

Also provided in the present disclosure are compounds of Formula (II)

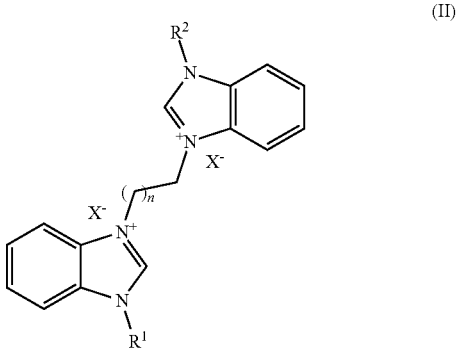

wherein:

$R^1$ and $R^2$ are each independently selected from $C_1$-$C_{10}$ alkyl, $C_1$-$C_{10}$ haloalkyl, $C_3$-$C_{10}$ cycloalkyl, aryl, 5-7 membered heteroaryl, 5-7 membered heterocycloalkyl, ($C_1$-$C_3$ alkylene)-($C_3$-$C_{10}$ cycloalkyl), ($C_1$-$C_3$ alkylene)-aryl, ($C_1$-$C_3$ alkylene)-(5-7 membered heteroaryl), and ($C_1$-$C_3$ alkylene)-(5-7 membered heterocycloalkyl);

X is selected from Cl, Br, and I; and n is 1 to 4.

In some embodiments of the compound of Formula (II), le is $C_1$-$C_{10}$ alkyl. In some embodiments of the compound of Formula (II), $R^1$ is $C_1$-$C_6$ alkyl. In some embodiments, $R^1$ is selected from methyl, ethyl, propyl, isopropyl, and butyl. In some embodiments, le is isopropyl. In some embodiments, the $C_1$-$C_6$ alkyl group is optionally substituted with one or more substituents independently selected from halogen, —CN, —OH, —NH$_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (II), $R^2$ is $C_1$-$C_{10}$ alkyl. In some embodiments of the compound of Formula (II), $R^2$ is $C_1$-$C_6$ alkyl. In some embodiments, $R^2$ is selected from methyl, ethyl, propyl, isopropyl, and butyl. In some embodiments, $R^2$ is isopropyl. In some embodiments, the $C_1$-$C_6$ alkyl group is optionally substituted with one or more substituents independently selected from halogen, —CN, —OH, —NH$_2$, C$_1$-C$_3$ alkyl, C$_1$-C$_3$ haloalkyl, C$_3$-C$_6$ cycloalkyl, —O—(C$_1$-C$_3$ alkyl), (C$_1$-C$_3$ alkylene)-O—(C$_1$-C$_3$ alkyl), and aryl.

In some embodiments of the compound of Formula (II), R$^1$ and R$^2$ are the same. In some embodiments, R$^1$ and R$^2$ are different.

In some embodiments of the compound of Formula (II), R$^1$ and R$^2$ are each independently C$_1$-C$_6$ alkyl. In some embodiments, R$^1$ and R$^2$ are each independently selected from methyl, ethyl, propyl, isopropyl, and butyl. In some embodiments, le is isopropyl and R$^2$ is isopropyl.

In some embodiments, X is selected from Cl, Br, and I. In some embodiments, X is Cl. In some embodiments, X is Br. In some embodiments, X is I.

In some embodiments of the compound of Formula (II), n is 1 to 4. In some embodiments, n is 1. In some embodiments, n is 2. In some embodiments, n is 3. In some embodiments, n is 4.

In some embodiments, the compound of Formula (II) is selected from:

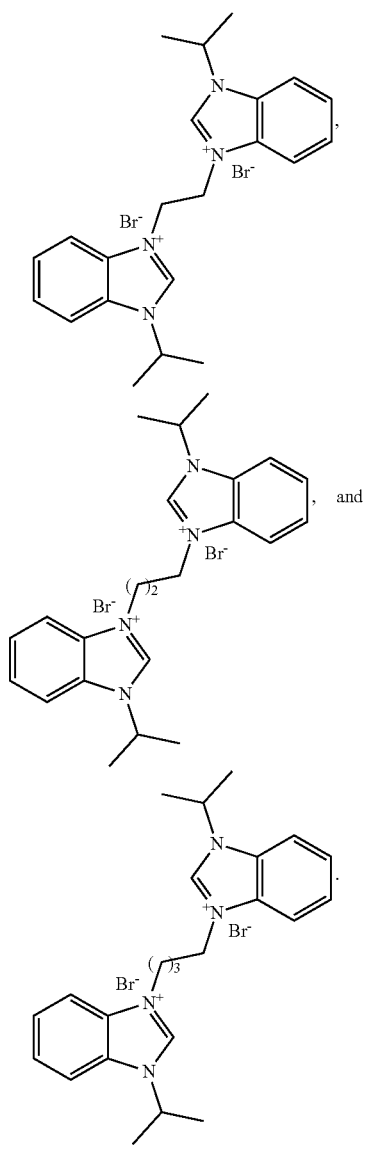

In some embodiments, the compound of Formula (II) is:

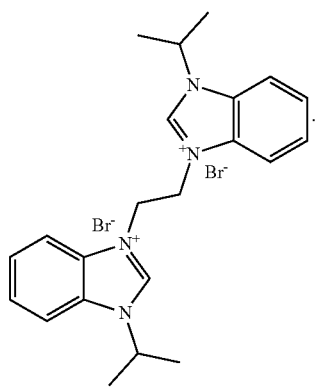 [SMILES: CC(C)n1c[n+](CC[n+]2cn(C(C)C)c3ccccc32)c2ccccc21 ; [Br-] ; [Br-]]

In some embodiments, the compound of Formula (II) is:

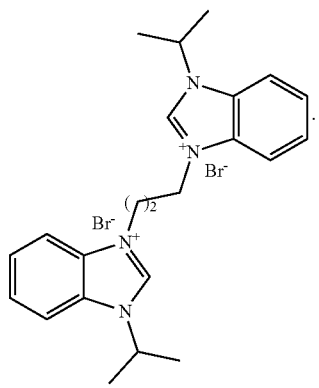

In some embodiments, the compound of Formula (II) is:

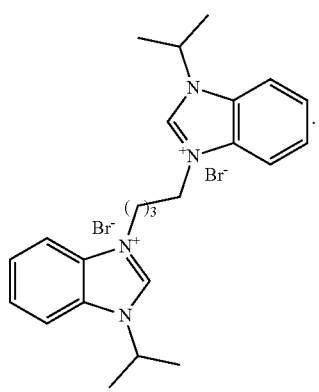

Method of Preparing Compounds of Formula (I) and Formula (II)

Also provided in the present disclosure are methods of preparing compounds of Formula (I) and Formula (II). In some embodiments, the method includes contacting a compound of Formula (II), such as a compound of Formula (II) as described in the present disclosure, with a palladium catalyst, to form a compound of Formula (I). In some embodiments, the compound of Formula (I) is isolated. In some embodiments, the compound of Formula (I) is purified.

In some embodiments, the palladium catalyst is palladium acetate.

In some embodiments, the compounds of Formula (I) are prepared according to the general scheme presented in Scheme 1, where $R^1$, $R^2$, X, and n are as described elsewhere in this disclosure.

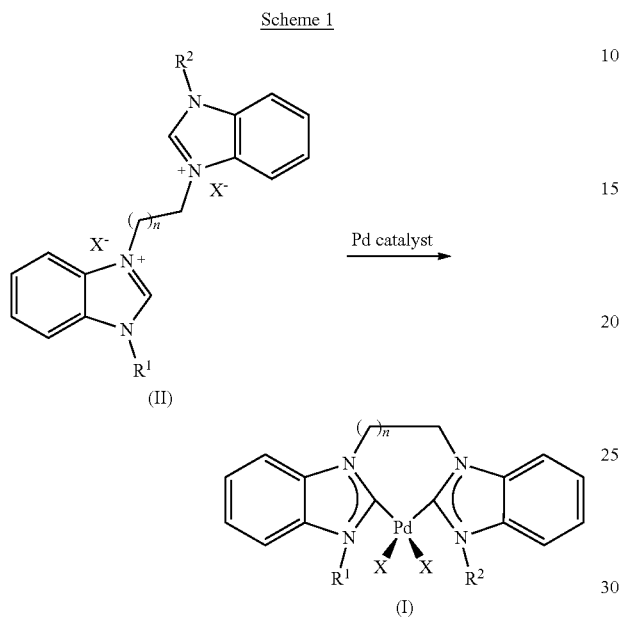

In some embodiments, the method includes preparing a compound of Formula (II). In some embodiments, the method includes reacting a substituted 1H-benzo[d]imidazole with an alkyl dihalide to form a compound of Formula (II). In some embodiments, the compound of Formula (II) is isolated. In some embodiments, the compound of Formula (II) is purified. In some embodiments, the compound of Formula (II) is isolated and purified prior to using in the method of preparing compounds of Formula (I).

In some embodiments, the alkyl dihalide is an alkyl group substituted with two halides. In some embodiments, each halide is independently selected from —F, —Cl, —Br, and —I. In some embodiments, the alkyl dihalide is an alkyl dibromide compound. In some embodiments, the alkyl group can range from one to six carbon atoms, such as one to four carbon atoms. In some embodiments, the alkyl group is selected from methyl, ethyl, propyl, butyl, pentyl, and hexyl. In some embodiments, the alkyl group is selected from methyl, ethyl, propyl, and butyl. In some embodiments, the alkyl dihalide is 1,2-dibromoethane. In some embodiments, the alkyl dihalide is 1,3-dibromopropane. In some embodiments, the alkyl dihalide is 1,4-dibromobutane.

In some embodiments, the compound of Formula (II) is prepared according to the general scheme presented in Scheme 2, where $R^1$, $R^2$, and X are as described elsewhere in this disclosure.

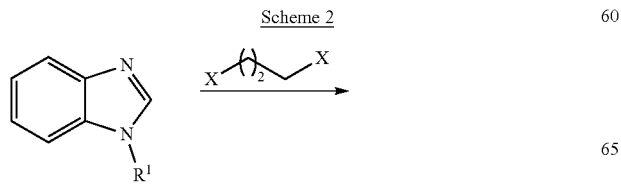

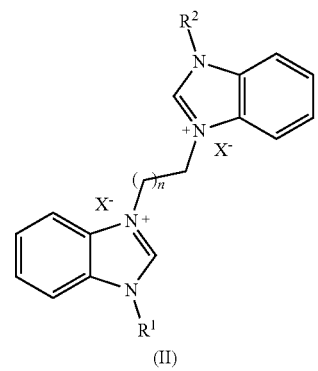

In some embodiments, the methods of the present disclosure are used to prepare a compound of Formula (I), where the compound of Formula (I) is selected from

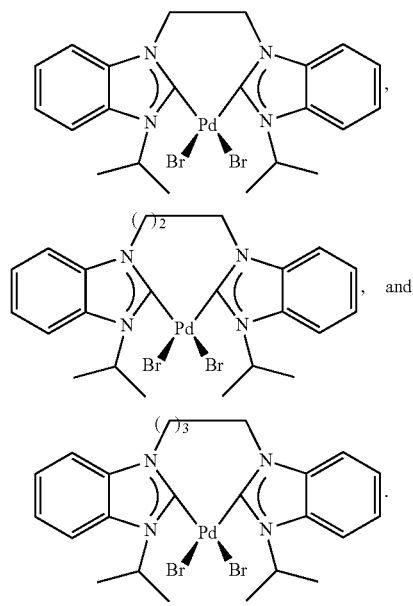

In some embodiments, the methods of present disclosure are used to prepare a compound of Formula (II), where the compound of Formula (II) is selected from

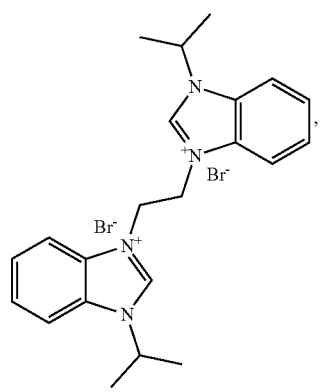

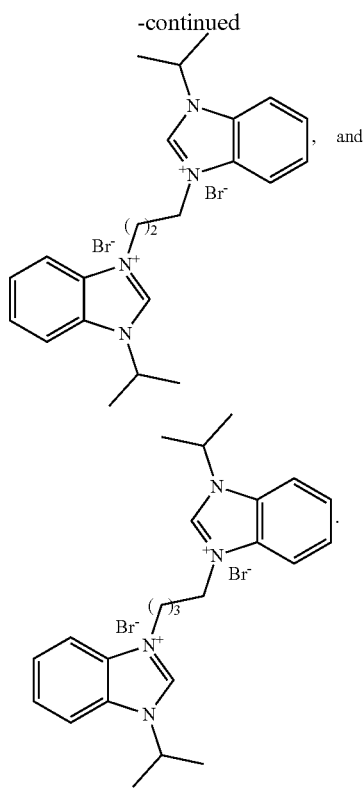

Methods of Preparing Biaryl Ketones and Biaryl Diketones

The compounds of Formula (I) of the present disclosure are useful as catalysts. For example, the compounds of Formula (I) can be used as catalysts for the synthesis of ketones and diketones, including biaryl ketones and biaryl diketones. In some embodiments, the compounds of Formula (I) are used as a catalyst in a carbonylative Suzuki-Miyaura coupling reaction. In some embodiments, the carbonylative Suzuki-Miyaura coupling reaction is between an aryl halide or aryl dihalide and an aryl boronic acid. In some embodiments, the carbonylative Suzuki-Miyaura coupling reaction is between an aryl bromide or aryl iodide and an aryl boronic acid.

In some embodiments, the biaryl ketones of the present disclosure are prepared according to the general scheme presented in Scheme 3, where R and R' can be any suitable substituent and X is as described elsewhere in this disclosure.

Scheme 3

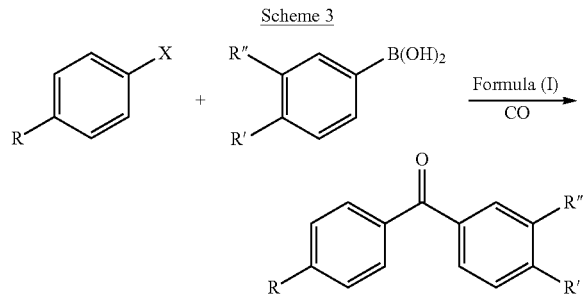

Thus, provided in the present disclosure is a method of preparing a biaryl ketone, the method including contacting an aryl halide or aryl dihalide and an aryl boronic acid with a compound of Formula (I), such as a compound of Formula (I) as described in the present disclosure, in the presence of a CO source.

In some embodiments, the method includes contacting an aryl halide and an aryl boronic acid with a compound of Formula (I) as described in the present disclosure in the presence of a CO source. In some embodiments, the aryl halide is a compound having the formula:

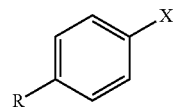

wherein:

X is selected from F, Cl, Br, and I; and

R is selected from H, $C_1$-$C_6$ alkyl, $C_1$-$C_6$ haloalkyl, —O—($C_1$-$C_6$ alkyl), aryl, CN, $NO_2$, —C(=O)H, and —C(=O)($C_1$-$C_6$ alkyl).

In some embodiments, X is F. In some embodiments, X is Cl. In some embodiments, X is Br. In some embodiments, X is I.

In some embodiments, R is selected from H, $C_1$-$C_6$ alkyl, $C_1$-$C_6$ haloalkyl, —O—($C_1$-$C_6$ alkyl), aryl, CN, $NO_2$, —C(=O)H, and —C(=O)($C_1$-$C_6$ alkyl). In some embodiments, R is selected from H, $C_1$-$C_3$ alkyl, $C_1$-$C_3$ haloalkyl, —O—($C_1$-$C_3$ alkyl), aryl, CN, $NO_2$, —C(=O)H, and —C(=O)($C_1$-$C_3$ alkyl). In some embodiments, R is selected from H, methyl, trifluoromethyl, —O—$CH_3$, CN, $NO_2$, —C(=O)H, and —C(=O)($CH_3$). In some embodiments, R is H. In some embodiments, R is $C_1$-$C_3$ alkyl. In some embodiments, R is methyl. In some embodiments, R is $C_1$-$C_3$ haloalkyl. In some embodiments, R is trifluoromethyl. In some embodiments, R is —O—($C_1$-$C_3$ alkyl). In some embodiments, R is —O—$CH_3$. In some embodiments, R is CN. In some embodiments, R is $NO_2$. In some embodiments, R is —C(=O)H. In some embodiments, R is —C(=O)($C_1$-$C_3$ alkyl). In some embodiments, R is C(=O)($CH_3$).

In some embodiments, the method includes contacting an aryl halide and an aryl boronic acid with a compound of Formula (I) as described in the present disclosure in the presence of a CO source. In some embodiments, the aryl boronic acid is a compound having the formula:

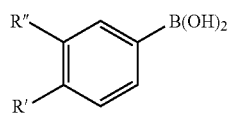

wherein:

R' is selected from H, $C_1$-$C_6$ alkyl, —O—($C_1$-$C_6$ alkyl), and aryl;

R" is selected from H, $C_1$-$C_6$ alkyl, —O—($C_1$-$C_6$ alkyl), and aryl; or

R' and R", taken together with the carbon atoms to which they are attached, form a 5-7 membered heterocycloalkyl ring.

In some embodiments, R' is selected from H, $C_1$-$C_6$ alkyl, —O—($C_1$-$C_6$ alkyl), and aryl. In some embodiments, R' is selected from H, $C_1$-$C_3$ alkyl, —O—($C_1$-$C_3$ alkyl), and aryl. In some embodiments, R' is selected from H and —O—$CH_3$.

In some embodiments, R" is selected from H, $C_1$-$C_6$ alkyl, —O—($C_1$-$C_6$ alkyl), and aryl. In some embodiments, R" is selected from H, $C_1$-$C_3$ alkyl, —O—($C_1$-$C_3$ alkyl), and aryl. In some embodiments, R" is H.

In some embodiments, R' and R", taken together with the carbon atoms to which they are attached, form a 5-7 membered heterocycloalkyl ring. In some embodiments, R' and R", taken together with the carbon atoms to which they are attached, form a 5 membered heterocycloalkyl ring. In some embodiments, R' and R", taken together with the carbon atoms to which they are attached, form a 5 membered heterocycloalkyl ring containing 2 oxygen atoms.

In some embodiments of the method of producing a biaryl ketone or biaryl diketone, the compound of Formula (I) is a compound of Formula (I) of the present disclosure. In some embodiments, the compound of Formula (I) is selected from:

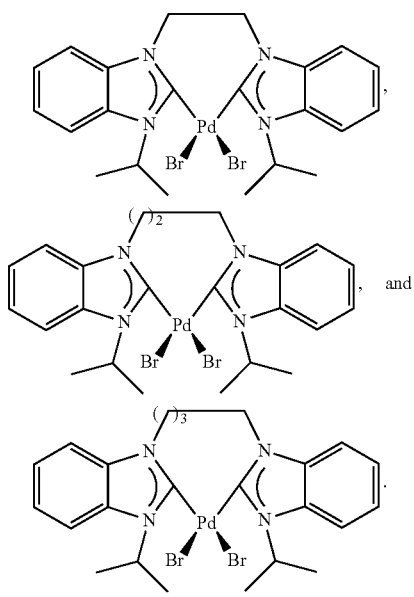

The compounds of Formula (I) have high catalytic efficiency and activity and allow for low catalyst loading. In some embodiments, less than or about 1 mol % of the compound of Formula (I) is required to catalyze a reaction, such as a carbonylative Suzuki-Miayura coupling reaction. In some embodiments, the amount of catalyst (compound of Formula (I)) used in the carbonylative Suzuki-Miayura coupling reaction is about 0.001 mol % to about 1 mol %, such as about 0.001 mol % to about 0.99 mol %, about 0.001 mol % to about 0.9 mol %, about 0.001 mol % to about 0.8 mol %, about 0.001 mol % to about 0.7 mol %, about 0.001 mol % to about 0.6 mol %, about 0.001 mol % to about 0.5 mol %, about 0.001 mol % to about 0.4 mol %, about 0.001 mol % to about 0.3 mol %, about 0.001 mol % to about 0.2 mol %, about 0.001 mol % to about 0.1 mol %, about 0.001 mol % to about 0.05 mol %, about 0.001 mol % to about 0.03 mol %, about 0.001 mol % to about 0.01 mol %, about 0.01 mol % to about 1 mol %, about 0.01 mol % to about 0.99 mol %, about 0.01 mol % to about 0.9 mol %, about 0.01 mol % to about 0.8 mol %, about 0.01 mol % to about 0.7 mol %, about 0.01 mol % to about 0.6 mol %, about 0.01 mol % to about 0.5 mol %, about 0.01 mol % to about 0.4 mol %, about 0.01 mol % to about 0.3 mol %, about 0.01 mol % to about 0.2 mol %, about 0.01 mol % to about 0.1 mol %, about 0.01 mol % to about 0.05 mol %, about 0.01 mol % to about 0.03 mol %, about 0.03 mol % to about 1 mol %, 0.03 mol % to about 0.99 mol %, about 0.03 mol % to about 0.9 mol %, about 0.03 mol % to about 0.8 mol %, about 0.03 mol % to about 0.7 mol %, about 0.03 mol % to about 0.6 mol %, about 0.03 mol % to about 0.5 mol %, about 0.03 mol % to about 0.4 mol %, about 0.03 mol % to about 0.3 mol %, about 0.03 mol % to about 0.2 mol %, about 0.03 mol % to about 0.1 mol %, about 0.03 mol % to about 0.05 mol %, about 0.05 mol % to about 1 mol %, 0.05 mol % to about 0.99 mol %, about 0.05 mol % to about 0.9 mol %, about 0.05 mol % to about 0.8 mol %, about 0.05 mol % to about 0.7 mol %, about 0.05 mol % to about 0.6 mol %, about 0.05 mol % to about 0.5 mol %, about 0.05 mol % to about 0.4 mol %, about 0.05 mol % to about 0.3 mol %, about 0.05 mol % to about 0.2 mol %, about 0.05 mol % to about 0.1 mol %, about 0.1 mol % to about 1 mol %, 0.1 mol % to about 0.99 mol %, about 0.1 mol % to about 0.9 mol %, about 0.1 mol % to about 0.8 mol %, about 0.1 mol % to about 0.7 mol %, about 0.1 mol % to about 0.6 mol %, about 0.1 mol % to about 0.5 mol %, about 0.1 mol % to about 0.4 mol %, about 0.1 mol % to about 0.3 mol %, about 0.1 mol % to about 0.2 mol %, about 0.2 mol % to about 1 mol %, 0.2 mol % to about 0.99 mol %, about 0.2 mol % to about 0.9 mol %, about 0.2 mol % to about 0.8 mol %, about 0.2 mol % to about 0.7 mol %, about 0.2 mol % to about 0.6 mol %, about 0.2 mol % to about 0.5 mol %, about 0.2 mol % to about 0.4 mol %, about 0.2 mol % to about 0.3 mol %, about 0.3 mol % to about 1 mol %, 0.3 mol % to about 0.99 mol %, about 0.3 mol % to about 0.9 mol %, about 0.3 mol % to about 0.8 mol %, about 0.3 mol % to about 0.7 mol %, about 0.3 mol % to about 0.6 mol %, about 0.3 mol % to about 0.5 mol %, about 0.3 mol % to about 0.4 mol %, about 0.4 mol % to about 1 mol %, 0.4 mol % to about 0.99 mol %, about 0.4 mol % to about 0.9 mol %, about 0.4 mol % to about 0.8 mol %, about 0.4 mol % to about 0.7 mol %, about 0.4 mol % to about 0.6 mol %, about 0.4 mol % to about 0.5 mol %, about 0.5 mol % to about 1 mol %, 0.5 mol % to about 0.99 mol %, about 0.5 mol % to about 0.9 mol %, about 0.5 mol % to about 0.8 mol %, about 0.5 mol % to about 0.7 mol %, about 0.5 mol % to about 0.6 mol %, about 0.6 mol % to about 1 mol %, 0.6 mol % to about 0.99 mol %, about 0.6 mol % to about 0.9 mol %, about 0.6 mol % to about 0.8 mol %, about 0.6 mol % to about 0.7 mol %, about 0.7 mol % to about 1 mol %, 0.7 mol % to about 0.99 mol %, about 0.7 mol % to about 0.9 mol %, about 0.7 mol % to about 0.8 mol %, about 0.8 mol % to about 1 mol %, 0.8 mol % to about 0.99 mol %, about 0.8 mol % to about 0.9 mol %, about 0.9 mol % to about 1 mol %, 0.9 mol % to about 0.99 mol %, or about 0.01 mol %, about 0.03 mol %, about 0.05 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 0.99 mol %, or about 1 mol %. In some embodiments, the compound of Formula (I) is present in an amount of about 0.001 mol % to about 1.0 mol %. In some embodiments, the compound of Formula (I) is present in an amount of about 0.001 mol % to about 0.5 mol %. In some embodiments, the compound of Formula (I) is present in an amount of about 0.001 mol % to about 0.05 mol %. In some embodiments, the compound of Formula (I) is present in an amount of about 0.005 mol % to about 0.015 mol %. In some embodiments, the compound of Formula (I) is present in an amount of about 0.01 mol %. Without wishing to be bound by any particular theory, it is believed that the increased catalytic activity of the compound of Formula (I) allows for the use of smaller amounts of the catalyst as compared to other palladium-based catalysts that have lower catalytic activity. For example, the amount of the compound of Formula (I) can be less than or about 1 mol %, which is less than the amount of about 1 mol % to about 5 mol % required by other palladium-based catalysts with lower catalytic activity.

In some embodiments of the methods of producing biaryl ketones and biaryl diketones as described in the present disclosure, any suitable CO source can be used. In some embodiments, the CO source is carbon monoxide gas. In some embodiments, the selectivity of the carbonylation product is controlled by the CO pressure. In some embodiments, the CO pressure is between about 50 psi and about 600 psi, such as about 50 psi to about 550 psi, about 50 psi to about 500 psi, about 50 psi to about 450 psi, about 50 psi to about 400 psi, about 50 psi to about 350 psi, about 50 psi to about 300 psi, about 50 psi to about 250 psi, about 50 psi to about 200 psi, about 50 psi to about 150 psi, about 50 psi to about 100 psi, about 100 psi to about 600 psi, about 100 psi to about 550 psi, about 100 psi to about 500 psi, about 100 psi to about 450 psi, about 100 psi to about 400 psi, about 100 psi to about 350 psi, about 100 psi to about 300 psi, about 100 psi to about 250 psi, about 100 psi to about 200 psi, about 100 psi to about 150 psi, about 150 psi to about 600 psi, about 150 psi to about 550 psi, about 150 psi to about 500 psi, about 150 psi to about 450 psi, about 150 psi to about 400 psi, about 150 psi to about 350 psi, about 150 psi to about 300 psi, about 150 psi to about 250 psi, about 150 psi to about 200 psi, about 200 psi to about 600 psi, about 200 psi to about 550 psi, about 200 psi to about 500 psi, about 200 psi to about 450 psi, about 200 psi to about 400 psi, about 200 psi to about 350 psi, about 200 psi to about 300 psi, about 200 psi to about 250 psi, about 250 psi to about 600 psi, about 250 psi to about 550 psi, about 250 psi to about 500 psi, about 250 psi to about 450 psi, about 250 psi to about 400 psi, about 250 psi to about 350 psi, about 250 psi to about 300 psi, about 300 psi to about 600 psi, about 300 psi to about 550 psi, about 300 psi to about 500 psi, about 300 psi to about 450 psi, about 300 psi to about 400 psi, about 300 psi to about 350 psi, about 350 psi to about 600 psi, about 350 psi to about 550 psi, about 350 psi to about 500 psi, about 350 psi to about 450 psi, about 350 psi to about 400 psi, about 400 psi to about 600 psi, about 400 psi to about 550 psi, about 400 psi to about 500 psi, about 400 psi to about 450 psi, about 450 psi to about 600 psi, about 450 psi to about 550 psi, about 450 psi to about 500 psi, about 500 psi to about 600 psi, about 500 psi to about 550 psi, about 550 psi to about 600 psi, or about 50 psi, about 100 psi, about 150 psi, about 200 psi, about 250 psi, about 300 psi, about 350 psi, about 400 psi, about 450 psi, about 500 psi, about 550 psi, or about 600 psi.

The biaryl ketones and biaryl diketones of the present disclosure have utility as precursors in the synthesis of products such as dyes and liquid crystals for electronic displays. The biaryl ketones and biaryl diketones of the present disclosure can also be used in the polymer industry. In some embodiments, the method produces a biaryl ketones having the formula:

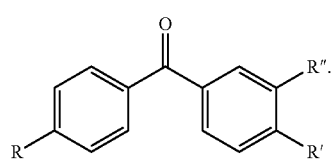

EXAMPLES

Example 1—Synthesis of Bridged Dibromo Bis(N-Heterocyclic Carbene)Palladium(II) (Pd(NHC)$_2$Br$_2$) Complexes A series of bridged dibromo bis(N-heterocyclic carbene) palladium(II) (Pd(NHC)$_2$Br$_2$) complexes (C$_1$, C$_2$, and C$_3$) were prepared in several steps from a substituted 1H-benzo[d]imidazole.

Synthesis of bridged NHC ligand precursors

Dibromido-(1,1'-propyl-3,3'-ethylenedibenzimidazoline) (L1), dibromido-(1,1'-propyl-3,3'-propylenedibenzimidazoline), (L2) and dibromido-(1,1'-propyl-3,3'-butylene dibenzimidazoline) (L3) were prepared in high yields by bridging two molecules of 1-isopropyl benzimidazole with the appropriate dibromo alkane by direct alkylation as shown in Scheme 4.

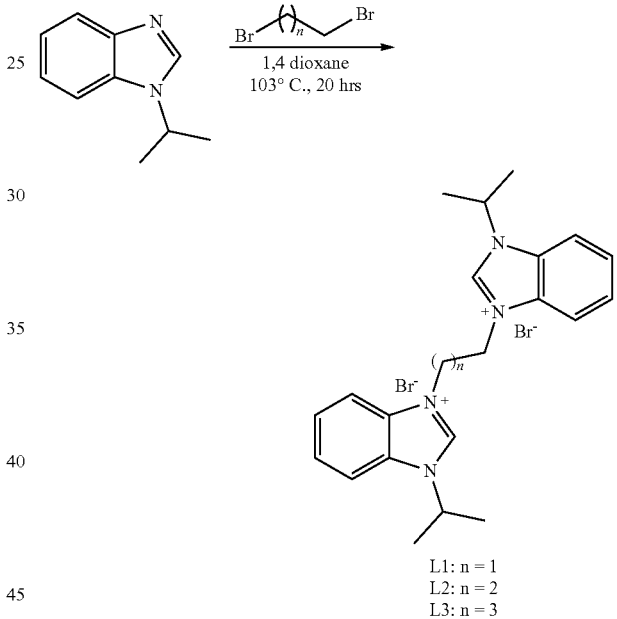

L1, L2, and L3 were prepared by according to the following general procedure. To a cleaned and dried 100 mL round bottom flask, 1-isopropyl benzimidazole (5.0 mmol) was introduced along with 2.5 mmol of a dibromoalkane (1,2-dibromoethane, 1,3-dibromopropane or 1,4-dibromobutane) and 35 mL of 1,4-dioxane. The reaction mixture was heated with stirring at 103° C. for 12 hrs. The product appeared as a precipitate which was filtered to remove the solvent and washed twice with 1,4-dioxane and then by toluene to remove any traces of reactants. The product was collected as a precipitate then characterized with spectroscopic techniques including $^1$H and $^{13}$C NMR and elemental analysis.

3,3'-Diisopropyl-1,1'-(ethane-1,2-diyl)dibenzimidazolium bromide (L1)

Yield=66%. Light yellow solid. $^1$H NMR (500 MHz, DMSO) δ (ppm): 9.85 (s, 2H, NCHN), 8.14-8.11 (m, 4H, Ar—H), 7.77-7.70 (m, 4H, Ar—H), 5.12 (m, 2H, NCH), 4.96-4.93 (m, 4H, NCH$_2$CH$_2$N), 1.52 [d, 12H, $^3$J=6.1 Hz (CH$_3$)$_2$]. $^{13}$C{$^1$H} NMR (500 MHz, DMSO) δ (ppm): 140.5

(NCN), 131.1, 130.4, 126.4, 126.5, 113.9, 113.6, (Ar—H), 50.5 (NCH), 46.1 (NCH$_2$),21.4 [NC(CH$_3$)$_2$]. Anal. Calcd for C$_{22}$H$_{30}$N$_4$Br$_2$ (508): C: 51.99%, H: 5.55%, N: 11.02%. Found: C: 51.94%, H: 5.73%, N: 11.23%, ESI: m/z 428 [M-Br]

3,3'-Diisopropyl-1,1'-(propane-1,3-diyl)dibenzimidazolium bromide (L2)

Yield=91%. White solid. $^1$H NMR (500 MHz, DMSO) δ (ppm): 9.83 (s, 2H, NCHN), 8.15-8.11 (m, 4H, Ar—H), 7.71-7.69 (m, 2H, Ar—H), 5.05 (sep, 2H, $^3$J=6.71 Hz, NCH), 4.67 (t, 4H, $^3$J=7.01 Hz, CH$_2$), 2.67 (qui, 2H, $^3$J=7.02 Hz, CH$_2$), 1.61 (d, 12H, $^3$J=6.7 Hz, NC(CH$_3$)$_2$).$^{13}$C{$^1$H} NMR (500 MHz, DMSO) δ (ppm); 140.7 (NCN), 131.3, 130.5, 126.7, 126.6, 114.1, 113.7, (Ar—H), 50.7 (NCH), 44.1 (NCH$_2$), 28.0 (CH$_2$), 21.6 (NC(CH$_3$)$_2$). Anal. Calcd for C$_{23}$H$_{30}$N$_4$Br$_2$ (522.3): C: 52.89%, H: 5.79%, N: 10.73%. Found: C: 52.37%, H: 5.8, %, N:10.97%; ESI: m/z 442 [M-Br$^-$]$^+$.

3,3'-Diisopropyl-1,1'-(butane-1,4-diyl)dibenzimidazolium bromide (L3)

Yield=76%. Light brown solid. $^1$H NMR (500 MHz, DMSO) δ (ppm): 10.05 (s, 2H, NCHN), 8.13-8.11 (m, 4H, Ar—H), 7.68 (dd, 4H, $^3$J1=6.1 Hz, $^3$J2=2.75 Hz, Ar—H), 5.05 (sept, 2H, $^3$J=6.71 Hz, NCH), 4.58 (m, 4H, NCH$_2$), 2.04-1.99 (m, 4H, CH$_2$), 1.62 [d, 12H, J=6.71 Hz (CH$_3$)$_2$]. $^{13}$C{$^1$H} NMR (500 MHz, DMSO) δ (ppm); 140.7 (NCN), 131.3, 130.6, 126.7, 126.6, 114.1, 113.8, (Ar—H), 50.7 (NCH), 46.3 (NCH$_2$), 25.6 (CH$_2$), 21.64 [NC(CH$_3$)$_2$]. Anal. Calcd for C$_{24}$H32N$_4$Br$_2$ (536.3): C: 53.74%, H: 6.01%, N: 10.45%. Found: C: 52.12%, H: 5.91%, N: 10.79%; ESI: m/z 456 [M-Br$^-$]$^+$.

Synthesis of palladium(II)-NHC-pyridine complexes

Dibromo bis(N-heterocyclic carbene)palladium(II) (Pd(NHC)$_2$Br$_2$) complexes C$_1$, C$_2$, and C$_3$ were prepared from L1, L2, and L3, respectively, as shown in Scheme 5.

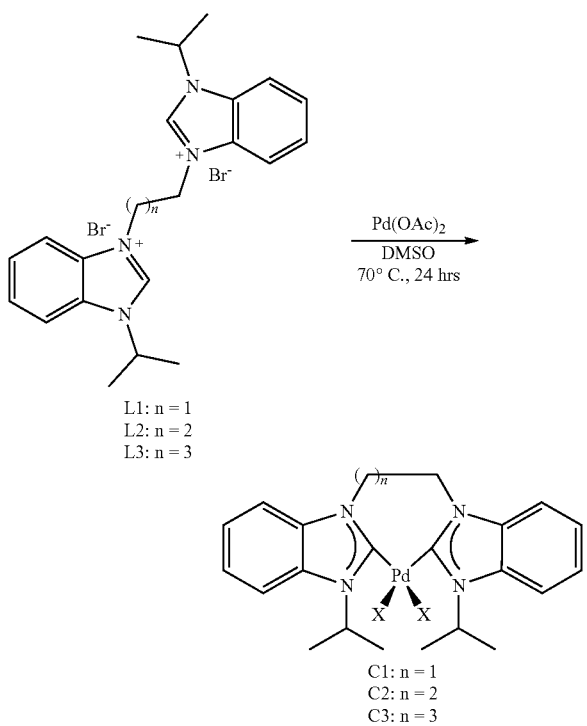

Scheme 5

L1: n = 1
L2: n = 2
L3: n = 3

C1: n = 1
C2: n = 2
C3: n = 3

C$_1$, C$_2$, and C$_3$ were prepared in high yields by reacting palladium acetate with 1 equivalent of the appropriate ligand NHC precursor L1, L2, or L3 in DMSO. To a cleaned and dried 50 mL round bottom flask, 1.00 mmol of the appropriate diazolium salts was dissolved in 15 mL of DMSO. Pd(OAc)$_2$ (226 mg, 1.00 mmol) was added to the DMSO solution. The orange solution was stirred for 24 h at 70° C. A white precipitate was formed. The mixture was filtered then washed with water then by hexane finally dried and collected. The formation of the new complexes was confirmed by the disappearance of the acidic C-2 protons of the benzimidazole rings, initially present in the N-substituted benzimidazolium salts due to palladation of the NHC ligand precursors.

Dibromido-(1,1'-diisopropyl-3,3'-ethylenedibenzimidazoline-2,2'-diylidene)palladium(II) (C1)

Yield=63%. Light Yellow solid. $^1$H NMR (500 MHz, DMSO) δ (ppm): 7.85 (d, 2H, $^3$J=6.72 Hz, Ar—H), 7.78 (d, 2H, $^3$J=6.4 Hz, Ar—H), 7.42-7.38 (m, 4H, Ar—H), 5.88-5.85 (m, 2H, NCH), 5.70-5.66 (m, 2H, CH$_2$), 5.08 (m, 2H, CH$_2$), 1.80 [d, 6H, $^3$J=6.71 Hz, NC(CH$_3$)$_2$], 1.62 [d, 6H, $^3$J=6.41 Hz, NC(CH$_3$)$_2$]; $^{13}$C{$^1$H} NMR (500 MHz, CD$_2$C$_{12}$) δ (ppm); 168.8 [Carbene signal (NC$_{binim}$N)], 134.9, 131.3, 123.4, 123.3, 112.9, 111.5 (Ar—H), 54.9 (NCH), 43.8 (NCH), 30.7 (CH$_2$), 20.6 [NC(CH$_3$)$_2$]. Anal. Calcd for C$_{22}$H26N$_4$Br$_2$Pd (612.7): C: 43.13%; H: 4.28%; N: 9.14%; Found: C: 43.21%; H: 4.25%; N: 9.63%. ESI: m/z 532 [M-Br]$^+$.

Dibromido-(1,1'-diisopropyl-3,3'-propylenedibenzimidazoline-2,2'-diylidene)palladium(II) (C2)

Yield=92%; White solid; $^1$H NMR (500 MHz, DMF) δ (ppm): 8.08 (d, 2H, $^3$J=8.24 Hz, Ar—H, integration not possible due to overlap of the complex with the solvent signal), 7.97 (d, 2H, $^3$J=8.24 Hz, Ar—H), 7.45-7.37 (m, 4H, Ar—H), 5.99 (m, 2H, NCH), 5.43 (m, 2H, CH$_2$), 5.11 (m, 2H, CH$_2$), 1.94 [d, 6H, $^3$J=6.71 Hz, NC(CH$_3$)$_2$], 1.78 [d, 6H, $^3$J=5.80 Hz, NC(CH$_3$)$_2$]. $^{13}$C{$^1$H} NMR (500 MHz, CD$_2$C$_{12}$) δ (ppm); 181 [Carbene signal (NC$_{binim}$N)], 135.2, 133.3, 132.3, 123.8, 123.7, 123.4, 123.1, 122.9, 113,2. 113, 110.7, 110.5 (Ar—H), 55.4 (NCH), 53.4 (NCH), 49.5 (NCH$_2$), 47.8 (NCH$_2$), 21.7 (CH$_2$), 30, 28.5, 22.1, 21.7, 21.3 [NC(CH$_3$)$_2$]. Anal. Calcd for C$_{23}$H28N$_4$Br$_2$Pd (626.74), C, 44.08%; H, 4.50%; N, 8.94%; Found: C: 43.86%, H: 4.25%, N: 8.63%. ESI: m/z 546.82 [M-Br]

Dibromido-(1,1'-diisopropyl-3,3'-butylenedibenzimidazoline-2,2'-diylidene)palladium(II) (C3)

Yield=68%. Orange solid. $^1$H NMR (400 MHz, CDCl$_3$) δ (ppm): 8.49 (d, 2H, $^3$J=7.28 Hz, Ar—H), 7.30 (d, 2H, $^3$J=7.44 Hz Ar—H), 7.17-7.14 (m, 4H, Ar—H). The signals of aromatic protons were not clearly observed due to overlap with solvent signals), 6.00-5.96 (m, 2H, NCH), 5.75-5.71 (m, 2H, NCH$_2$), 4.45-4.41 (m, 2H, NCH$_2$), 1.80-1.45 (m, 4H, NCH$_2$CH$_2$. The signals of methylene protons were not clearly observed due to overlap with the isopropyl methyl signals), 1.74 [d, 6H, $^3$J=6.56 Hz (CH$_3$)$_2$], 1.69 [d, 6H, $^3$J=7.16 Hz (CH$_3$)$_2$]. $^{13}$C{$^1$H} NMR (500 MHz, CD$_2$C$_{12}$) δ (ppm); 181.1 [Carbene signal (NC$_{binim}$N)], 135.9, 132.9, 122.9, 122.8, 112.9, 111.0, (Ar—H), 48.2 (NCH), 30.1 (NCH$_2$), 27.7 (CH$_2$), 21.2 [NC(CH$_3$)$_2$]. Anal. Calcd for C$_{24}$H$_{30}$N$_4$Br$_2$Pd (640): C: 44.99%; H: 4.72%, N: 8.74%; Found: C: 44.78%, H: 4.89%, N: 8.53%. ESI: m/z 560 [M-Br]$^+$ Example 2—Carbonylative Suzuki-Miyaura Coupling Reactions The dibromo bis(N-heterocyclic carbene)palladium(II) (Pd(NHC)$_2$Br$_2$) complexes C$_1$, C$_2$, and C$_3$ prepared according to Example 1 were used in carbonylative Suzuki-Miyaura coupling reactions to produce a series of biaryl ketones. The $Pd(NHC)_2Br_2$ catalysts displayed high catalytic activity with low catalyst loading. The reactions required only 0.01 mol % of the $Pd(NHC)_2Br_2$ complex and produced biaryl ketones in high yield.

Carbonylative Suzuki-Miyaura coupling reaction of iodoanisole with arylboronic acid A biaryl ketone was synthesized by reacting iodoanisole with arylboronic acid in the presence of a catalyst including $Pd(NHC)_2Br_2$ (C1, C2, C3), or a comparative catalyst according to the process described in the synthesis of biaryl ketones above, using catalyst (0.01 mol %), iodoanisole (1.0 mmol), arylboronic acid (1.2 mmol), base (2.0 mmol), toluene (5.0 mL), and CO (200 psi). Scheme 6 and Table 1 illustrate the synthesis and results.

As can be seen, biaryl ketones were produced in higher yields when catalysts C1, C2, or C3 were used as compared to traditional palladium catalysts.

Scheme 6

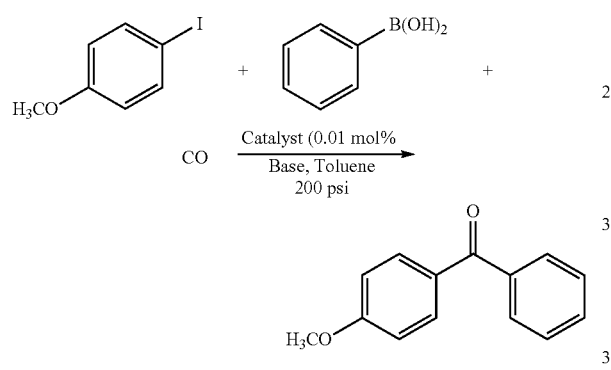

TABLE 1

| Entry | T (° C.) | Base | Catalyst (0.01 mol %) | Time (h) | Isolated Yield (%) |
|---|---|---|---|---|---|
| 1 | 120 | $K_2CO_3$ | C1 | 6 | 99 |
| 2 | 120 | $K_2CO_3$ | C1 | 3 | 98 |

TABLE 1-continued

| Entry | T (° C.) | Base | Catalyst (0.01 mol %) | Time (h) | Isolated Yield (%) |
|---|---|---|---|---|---|
| 3 | 120 | $K_2CO_3$ | C1 | 1 | 61 |
| 4 | 80 | $K_2CO_3$ | C1 | 3 | 58 |
| 5 | 100 | $K_2CO_3$ | C1 | 3 | 82 |
| 6 | 120 | — | C1 | 3 | traces |
| 7 | 120 | KOH | C1 | 3 | 87 |
| 8 | 120 | $Et_3N$ | C1 | 3 | 12 |
| 9 | 120 | $K_2CO_3$ | C2 | 3 | 95 |
| 10 | 120 | $K_2CO_3$ | C3 | 3 | 89 |
| 11 | 120 | $K_2CO_3$ | $Pd(OAc)_2/L1^a$ | 3 | 82 |
| 12 | 120 | $K_2CO_3$ | $Pd(OAc)_2$ | 3 | 75 |
| 13 | 120 | $K_2CO_3$ | $Pd(C_6H_5CN)_2Cl_2$ | 3 | 62 |
| 14 | 120 | $K_2CO_3$ | $Pd(CN)_2$ | 3 | 70 |
| 15 | 120 | $K_2CO_3$ | $PdBr_2$ | 3 | 68 |
| 16 | 120 | $K_2CO_3$ | $PdI_2$ | 3 | 71 |
| 17 | 120 | $K_2CO_3$ | $PdCl_2$ | 3 | 66 |
| 18 | 120 | $K_2CO_3$ | $Pd(PPh_3)_3Cl_2$ | 3 | 72 |

$^a$L1(010 mol %)

Synthesis of biaryl ketones using C1

A series of biaryl ketones was synthesized by reacting aryl iodides with aryl boronic acids in the presence of the C1 catalyst as shown in Scheme 7 and Table 2.

Scheme 7

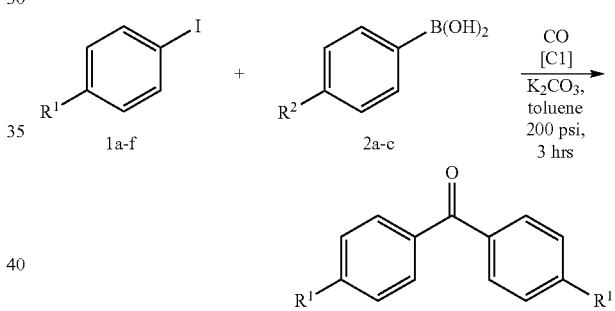

TABLE 2

| Entry | Aryl iodide | Aryl boronic acid | Product 3 | Isolated Yield (%) |
|---|---|---|---|---|
| 1 | 1a | 2a | 3a | 98 |
| 2 | 1b | 2a | 3b | 95 |

TABLE 2-continued

| Entry | Aryl iodide | Aryl boronic acid | Product 3 | Isolated Yield (%) |
|---|---|---|---|---|
| 3 | 1c (4-methylphenyl iodide) | 2a (phenylboronic acid) | 3c (4-methylbenzophenone) | 93 |
| 4 | 1d (4-acetylphenyl iodide) | 2a (phenylboronic acid) | 3d (4-acetylbenzophenone) | 99 |
| 5 | 1e (4-nitrophenyl iodide) | 2a (phenylboronic acid) | 3e (4-nitrobenzophenone) | 96 |
| 6 | 1f (4-cyanophenyl iodide) | 2a (phenylboronic acid) | 3f (4-cyanobenzophenone) | 97 |
| 7 | 1e (4-nitrophenyl iodide) | 2b (4-methoxyphenylboronic acid) | 3g (4-nitro-4′-methoxybenzophenone) | 98 |
| 8 | 1b (phenyl iodide) | 2b (4-methoxyphenylboronic acid) | 3h (4-methoxybenzophenone) | 96 |
| 9 | 1a (4-methoxyphenyl iodide) | 2b (4-methoxyphenylboronic acid) | 3i (4,4′-dimethoxybenzophenone) | 97 |

TABLE 2-continued

| Entry | Aryl iodide | Aryl boronic acid | Product 3 | Isolated Yield (%) |
|---|---|---|---|---|
| 10 | 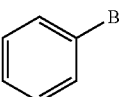 1a | 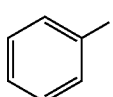 2c | 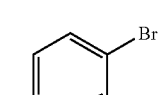 3j | 95 |

The carbonylative coupling reaction was performed by reacting aryl iodides 1a-1f with aryl boronic acids 2a-2c in the presence of 0.01 mol % of C1, with 2.0 equivalents of $K_2CO_3$, 5 mL of toluene, 200 psi CO, at 120° C. for 3 hrs. Biaryl ketones 3a-3j were produced in excellent yields (93-98%) via the carbonylative Suzuki-Miyaura coupling reaction.

Carbonylative Suzuki-Miyaura coupling reaction of aryl bromides with arylboronic acid by C1

Carbonylative Suzuki-Miyaura coupling reactions of aryl bromides with aryl boronic acids catalyzed by the palladium catalyst C1 in the presence of two equivalent of triarylphosphine, where the selectivity in the carbonylation product of was controlled by the CO pressure were also performed as shown in Scheme 8 and Table 3. The following components and conditions were used: C1 (1.0 mol %), $PPh_3$ (2.0 mol %), aryl bromide (1.0 mmol), aryl boronic acid (1.2 mmol), $K_2CO_3$ (2.0 mmol), toluene (5.0 mL), CO (200 psi), 120° C., 20 hrs.

Scheme 8

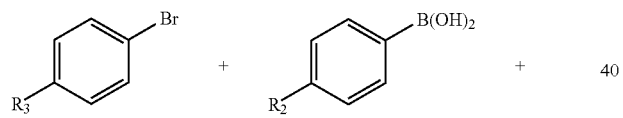

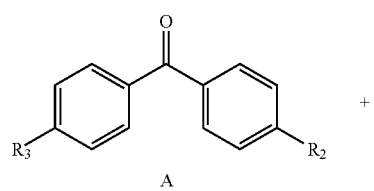

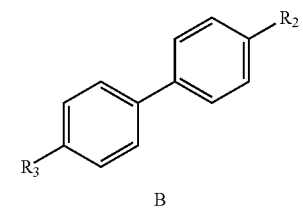

TABLE 3

| Entry | R3 | R2 | Conv. %[a] | Product Distribution %[a] | |
|---|---|---|---|---|---|
| | | | | A | B |
| 1 | 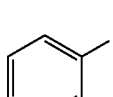 Br | 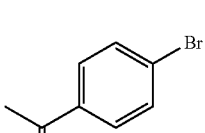 $B(OH)_2$ | 0 | Traces | Traces |
| 2 | $H_3C$-C6H4-Br | C6H5-$B(OH)_2$ | 0 | Traces | Traces |
| 3[b] | $CH_3C(O)$-C6H4-Br | C6H5-$B(OH)_2$ | 53 | 81 | 19 |

TABLE 3-continued

| Entry | R3 | R2 | Conv. %[a] | Product Distribution %[a] | |
|---|---|---|---|---|---|
| | | | | A | B |
| 4 | 4-bromoacetophenone | phenylboronic acid | 97 | 97 | 3 |
| 5[c] | 4-bromoacetophenone | phenylboronic acid | 50 | 32 | 68 |
| 6[d] | 4-bromoacetophenone | phenylboronic acid | 67 | 41 | 59 |
| 7 | 4-bromoacetophenone | 4-methoxyphenylboronic acid | 84 | 100 | 0.0 |
| 8[e] | 4-bromoacetophenone | 4-methoxyphenylboronic acid | 95 | 100 | 0.0 |
| 9[e] | 4-bromoacetophenone | benzo[d][1,3]dioxol-5-ylboronic acid | 92 | 100 | 0.0 |
| 10 | 4-bromobenzaldehyde | phenylboronic acid | 97 | 78 | 22 |
| 11[f] | 4-bromobenzaldehyde | phenylboronic acid | 88 | 89 | 11 |
| 12[g] | 4-bromobenzaldehyde | phenylboronic acid | 92 | 94 | 6 |

TABLE 3-continued

| Entry | R3 | R2 | Conv. %[a] | Product Distribution %[a] | |
|---|---|---|---|---|---|
| | | | | A | B |
| 13 | 4-CF3-C6H4-Br | C6H5-B(OH)2 | 93 | 58 | 42 |
| 14[f] | 4-CF3-C6H4-Br | C6H5-B(OH)2 | 61 | 82 | 18 |
| 15[g] | 4-CF3-C6H4-Br | C6H5-B(OH)2 | 90 | 91 | 9 |
| 16[g] | 4-NC-C6H4-Br | C6H5-B(OH)2 | 94 | 93 | 7 |

[a]Conversion was measured by GC.
[b]Cl (0.5 mol %), PPh3 (1.0 mol %),
[c]Pd(OAc)2
[d]Pd(PPh3)2Cl2
[e]Acetonitrile was used as solvent.
[f]400 psi
[g]600 psi

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a biaryl ketone, comprising contacting an aryl halide and an aryl boronic acid with a compound of Formula (I) in the presence of a CO source, wherein the compound of Formula (I) has the structure:

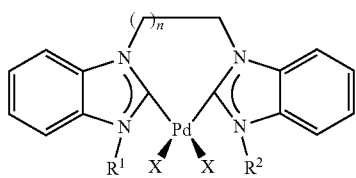

(I)

wherein:
$R^1$ and $R^2$ are each independently selected from $C_1$-$C_{10}$ alkyl, $C_1$-$C_{10}$ haloalkyl, $C_3$-$C_{10}$ cycloalkyl, aryl, 5-7 membered heteroaryl, 5-7 membered heterocycloalkyl, ($C_1$-$C_3$ alkylene)-($C_3$-$C_{10}$ cycloalkyl), ($C_1$-$C_3$ alkylene)-aryl, ($C_1$-$C_3$ alkylene)-(5-7 membered heteroaryl), and ($C_1$-$C_3$ alkylene)-(5-7 membered heterocycloalkyl);
X is selected from Cl, Br, and I;
n is 1 to 4; and
wherein the compound of Formula (I) is present in an amount of about 0.001 mol % to about 1.0 mol %.

2. The method of claim 1, wherein $R^1$ and $R^2$ are each independently $C_1$-$C_6$ alkyl.

3. The method of claim 2, wherein $R^1$ and $R^2$ are each independently selected from methyl, ethyl, propyl, isopropyl, and butyl.

4. The method of claim 3, wherein $R^1$ and $R^2$ are each isopropyl.

5. The method of claim 1, wherein X is Br.

6. The method of claim 1, wherein n is 1.

7. The method of claim 1, wherein n is 2.

8. The method of claim 1, wherein n is 3.

9. The method of claim 1, wherein the compound of Formula (I) is selected from:

,

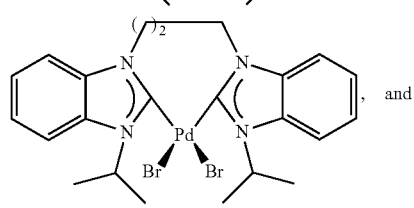

, and

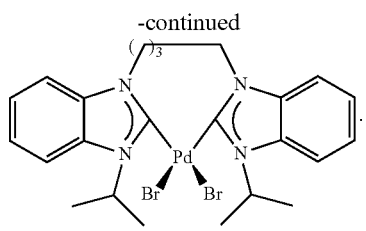

10. The method of claim 1, wherein the aryl halide is a compound having the formula:

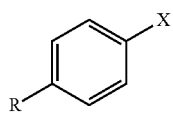

wherein:

X is selected from F, Cl, Br, and I; and

R is selected from H, $C_1$-$C_6$ alkyl, $C_1$-$C_6$ haloalkyl, —O—($C_1$-$C_6$ alkyl), CN, $NO_2$, —C(=O)H, and —C(=O)($C_1$-$C_6$ alkyl).

11. The method of claim 10, wherein X is I.

12. The method of claim 10, wherein X is Br.

13. The method of claim 10, wherein R is selected from H, $C_1$-$C_3$ alkyl, $C_1$-$C_3$ haloalkyl, —O—($C_1$-$C_3$ alkyl), CN, $NO_2$, —C(=O)H, and —C(=O)($C_1$-$C_3$ alkyl).

14. The method of claim 13, wherein R is selected from H, methyl, trifluoromethyl, —O—$CH_3$, CN, $NO_2$, —C(=O)H, and —C(=O)($CH_3$).

15. The method of claim 1, wherein the aryl boronic acid is a compound having the formula:

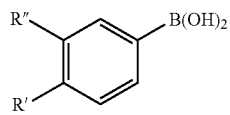

wherein:

R' is selected from H, $C_1$-$C_6$ alkyl, and —O—($C_1$-$C_6$ alkyl);

R" is selected from H, $C_1$-$C_6$ alkyl, and —O—($C_1$-$C_6$ alkyl); or

R' and R", taken together with the carbon atoms to which they are attached, form a 5-7 membered heterocycloalkyl ring.

16. The method of claim 15, wherein R' is selected from H and —O—$CH_3$.

17. The method of claim 15, wherein R" is H.

18. The method of claim 15, wherein R' and R", taken together with the carbon atoms to which they are attached, form a 5-membered heterocycloalkyl ring containing 2 oxygen atoms.

19. The method of claim 1, wherein the biaryl ketone is a compound having the formula:

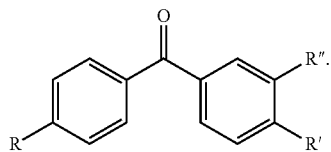

20. The method of claim 1, wherein the compound of Formula (I) is present in an amount of about 0.05 mol % to about 0.015 mol %.

21. The method of claim 1, wherein the compound of Formula (I) is present in an amount of about 0.01 mol %.

* * * * *